United States Patent
Lau et al.

(10) Patent No.: US 9,283,317 B2
(45) Date of Patent: Mar. 15, 2016

(54) FUNCTIONAL BROWN ADIPOSE TISSUE IMAGING TECHNIQUE

(71) Applicant: General Electric Company, Schenectady, NY (US)

(72) Inventors: Angus Zoen Lau, Headington (GB); Albert Po-Fu Chen, Toronto (CA); Charles H. Cunningham, Toronto (CA)

(73) Assignee: General Electric Company, Schenectady, NY (US)

( * ) Notice: Subject to any disclaimer, the term of this patent is extended or adjusted under 35 U.S.C. 154(b) by 239 days.

(21) Appl. No.: 13/841,945

(22) Filed: Mar. 15, 2013

(65) Prior Publication Data

US 2014/0275969 A1    Sep. 18, 2014

(51) Int. Cl.
A61B 6/00 (2006.01)
A61M 5/00 (2006.01)
A61B 5/055 (2006.01)
G01R 33/56 (2006.01)

(52) U.S. Cl.
CPC .............. *A61M 5/007* (2013.01); *A61B 5/055* (2013.01); *G01R 33/5601* (2013.01)

(58) Field of Classification Search
CPC .... A61M 5/007; A61B 5/055; G01R 33/5601
USPC .......... 600/407–430; 424/1.11, 1.65, 9.1, 9.6, 424/93.21, 93.7, 400; 378/98.11, 8
See application file for complete search history.

(56) References Cited

U.S. PATENT DOCUMENTS

| 5,214,382 A * | 5/1993 | Harms et al. ................. 324/309 |
| 2004/0022359 A1 * | 2/2004 | Acharya et al. ............ 378/98.11 |
| 2005/0065430 A1 * | 3/2005 | Wiethoff et al. .............. 600/413 |
| 2006/0052690 A1 * | 3/2006 | Sirohey et al. ................ 600/420 |
| 2011/0116697 A1 * | 5/2011 | Dafni et al. ................... 382/131 |
| 2012/0321671 A1 * | 12/2012 | Boyden et al. ................. 424/400 |
| 2014/0037046 A1 * | 2/2014 | Grass et al. ...................... 378/8 |
| 2014/0178293 A1 * | 6/2014 | Davis et al. ................. 424/1.11 |
| 2014/0199239 A1 * | 7/2014 | Bertozzi et al. ............. 424/1.65 |

FOREIGN PATENT DOCUMENTS

| WO | 2008008075 A3 | 1/2008 |
| WO | 2012098226 A2 | 7/2012 |

OTHER PUBLICATIONS

Magnetic Resonance in Medicine: Official Journal of the Society of Magnetic Resonance in Medicine (ETOCRN184339934).
International Journal of Obesity (ETOCRN345177806).
The GB Combined Search & Exam Report issued in connection with corresponding GB Application No. 1407580.8 dated Sep. 26, 2014.

* cited by examiner

*Primary Examiner* — Sanjay Cattungal
(74) *Attorney, Agent, or Firm* — William K. Baxter; General Electric Company

(57) ABSTRACT

Disclosed embodiments for assessing brown adipose tissue use imaging of metabolic contrast agents. For example, activated brown adipose tissue may be assessed by evaluating a difference in production of the hyperpolarized $^{13}C$ metabolic contrast agent from a pre-polarized $^{13}C$ metabolic contrast agent precursor before and after exposure of the subject to an activating event or agent. In one embodiment, the subject is given a dose of norepinephrine, and the production of the hyperpolarized $^{13}C$ metabolic contrast agent before and after the dose is assessed.

19 Claims, 5 Drawing Sheets
(2 of 5 Drawing Sheet(s) Filed in Color)

FUNCTIONAL BROWN ADIPOSE TISSUE IMAGING TECHNIQUE

BACKGROUND

The present techniques relate generally to identification and/or characterization of brown adipose tissue. More specifically, the techniques relate to methods and systems for non-invasive imaging of brown adipose tissue that identify functional brown adipose tissue.

Brown adipose tissue (BAT) represents a promising pharmacological target for the treatment of obesity. Identification of BAT tissue in vivo may be used to evaluate new therapies aimed at inducing the production of more BAT or activating BAT in humans. BAT may be identified in vivo using anatomical $^1$H MRI scans designed to separate water and fat content in tissue, but these techniques do not assess whether the tissue is functional, e.g., activated. Other approaches for assessing the functional state of BAT in vivo include radio-labeled FDG-PET imaging, methods assessing perfusion such as contrast-enhanced ultrasound, $^1$H MRI (BOLD) methods assessing oxygenation-related signal changes in BAT, as well as thermal imaging methods assessing skin temperature changes with BAT activation. Of these methods, the only current clinically used technique is FDG-PET, which involves ionizing radiation.

BRIEF DESCRIPTION

Provided herein are non-invasive and ionizing radiation-free assessment techniques for characterization of BAT and measurement of the volume of BAT. In certain embodiments, the dynamic nuclear polarization (DNP) and dissolution technique involve an injectable $^{13}$C-labeled metabolic contrast agent that can be used to non-invasively study metabolic processes occurring in real-time and in vivo. For example, in one example, activated BAT is characterized by increased oxidative phosphorylation contributing to futile cycling of ATP through the mitochondrial uncoupling protein 1 (UCP1). As a result of this increased oxidative phosphorylation, the metabolic change between inactive and activated BAT may be detected by increased conversion of a [1-$^{13}$C] pyruvate metabolic contrast agent into its downstream metabolic products $^{13}$C-bicarbonate and [1-$^{13}$C] lactate. In another embodiment, the total volume of BAT may be measured without a baseline measurement, by computing the volume of adipose tissue in which there is evidence of metabolic conversion of the injected $^{13}$C-labeled substrate. For example, the spatial distribution and volume of these $^{13}$C-labeled compounds can then be visualized using a dynamic volumetric, chemical-shift specific $^{13}$C imaging sequence.

In a first embodiment, a method for measuring the volume of brown adipose tissue includes magnetic resonance imaging of the fat/water distribution within a subject, followed by imaging using $^3$C-labeled compounds to detect regions of metabolic activity within adipose tissue. The signal from this brown adipose tissue may be enhanced by exposing the subject to an activating stimulus, such as a cold-water blanket around the body or a drug such as norepinephrine.

In another embodiment, a method for detecting brown adipose tissue includes acquiring one or more baseline images of an adipose tissue of the subject representative of a relative level of a pre-polarized metabolic contrast agent, its metabolic products, or a combination thereof; and determining a presence of brown adipose tissue based at least in part on the images In another embodiment, a method for detecting activated brown adipose tissue includes acquiring a baseline tissue image of a subject representative of a concentration of a hyperpolarized metabolic contrast agent; acquiring an activated tissue image of a subject representative of a concentration of a hyperpolarized metabolic contrast agent after exposing the subject to a brown adipose tissue activating agent or event; determining a difference between the baseline tissue image and the activated tissue image; and determining a presence of brown adipose tissue activation based at least in part on the difference.

In another embodiment, an imaging system includes a processor configured to receive and process image data. The processor is configured to: receive a baseline tissue image of a subject with a $^{13}$C metabolic contrast agent in a bloodstream of the subject; receive an activated tissue image of a subject with the $^{13}$C metabolic contrast agent in the bloodstream of the subject after exposing the subject to a brown adipose tissue activating agent or event, wherein the baseline tissue image and the activated tissue image are representative of a concentration of one or more hyperpolarized $^{13}$C products of the $^{13}$C metabolic contrast agent; determine a difference between the baseline tissue image and the activated tissue image; and determine a level or presence of brown adipose tissue activation based at least in part on the difference. The system also includes a display coupled to the processor and configured to provide an indication related to the level or presence of brown adipose tissue activation.

In another embodiment, injecting a pre-polarized $^{13}$C metabolic contrast agent into a bloodstream of a subject; exposing the subject to a brown adipose tissue activating agent or event; and providing one or more inputs to an imaging system to instruct the imaging system to obtain a plurality of images of the subject, wherein the images comprise a baseline tissue image and an activated tissue of the subject, wherein the baseline image is obtained before exposing the subject to the brown adipose tissue activating agent or event and the activated tissue image is acquired after exposing the subject to the brown adipose tissue activating agent or event.

DRAWINGS

The file of this patent contains at least one drawing executed in color. Copies of this patent with color drawing(s) will be provided by the U.S. Patent and Trademark Office upon request and payment of the necessary fee.

DETAILED DESCRIPTION

Figure 1:
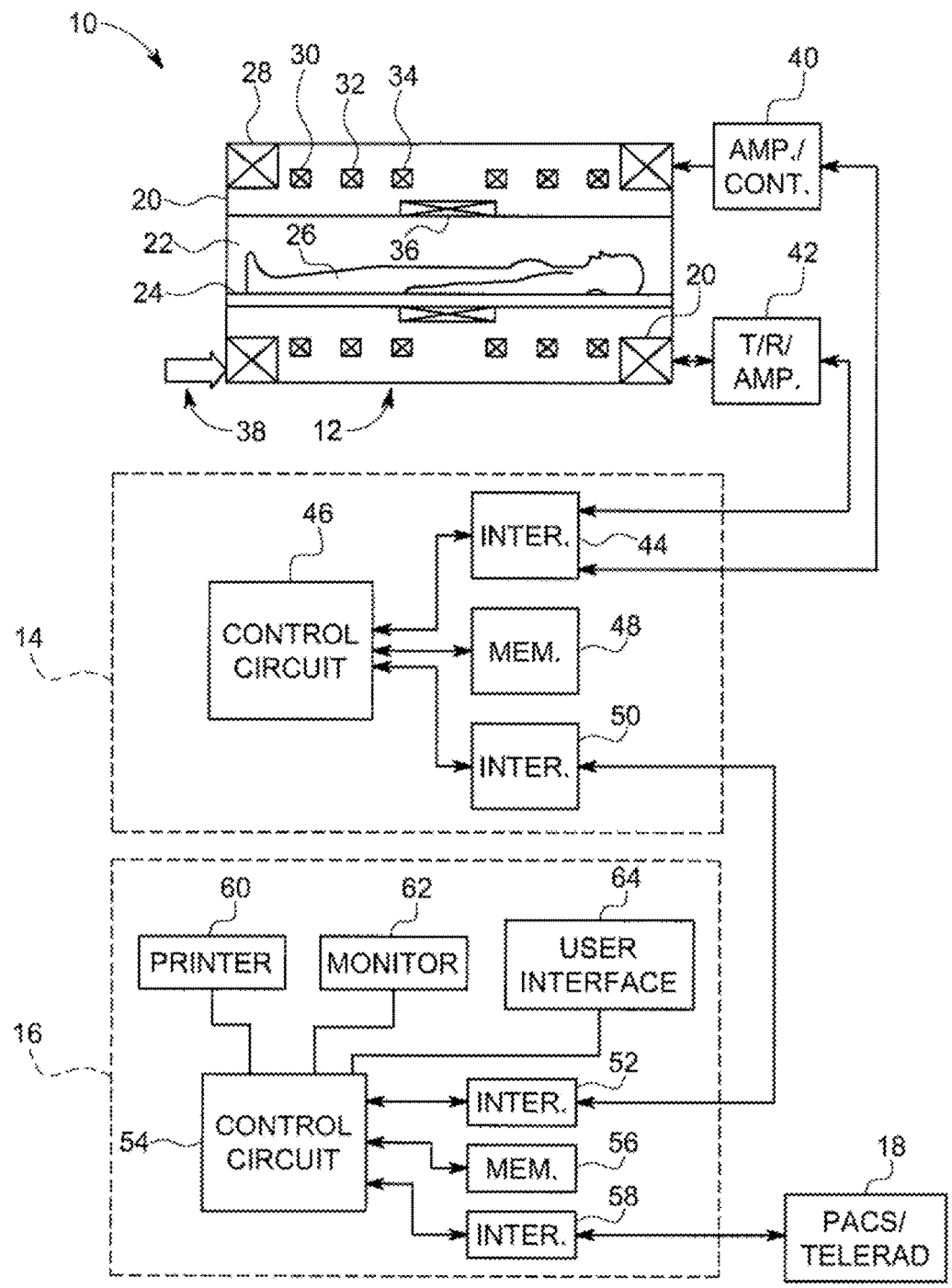
FIG. 1 is a diagrammatic illustration of an embodiment of a magnetic resonance imaging system configured to perform the image acquisition according to an embodiment.

As provided herein, imaging of a hyperpolarized metabolic contrast agent may be used to non-invasively identify activated deposits of brown adipose tissue in vivo. In certain embodiments, tissue regions containing activated brown adipose tissue, stimulated by norepinephrine injection, can be detected by increased conversion of a metabolic contrast agent, such as a pre-polarized [1-$^{13}$C] pyruvate, into its downstream products, such as $^{13}$C-bicarbonate and [1-$^{13}$C] lactate, among others. Because $^{13}$C is a stable isotope, the radiation-free nature of this imaging test may provide benefits for clinical implementation. In one embodiment, hyperpolarized $^{13}$C imaging methods may be used to identify and assess the functional state of BAT in vivo, without the use of ionizing radiation. For example, functional BAT assessment following activation of the BAT (e.g., via norepinephrine stimulation) may be accomplished by detecting increased conversion of pre-polarized [1-$^{13}$C] pyruvate into its downstream products $^{13}$C-bicarbonate and [1-$^{13}$C] lactate.

In adult humans, BAT has been found in small and variable-sized deposits in the cervical neck and supraclavicular region, chest, as well as abdomen, and disseminated brown adipocytes may also be found within subcutaneous white adipose tissue. BAT contributes to non-shivering thermogenesis, a process that is activated by cold exposure as well as by beta-adrenergic stimulation, but new agents that specifically target BAT activation may be better tolerated and more efficient in stimulating BAT activity. Non-invasive, radiation-free imaging tests to assess functional BAT in vivo may be used to assess the development of new therapies aimed at inducing the production of more BAT or activating BAT in humans. Accordingly, the present techniques may be used in conjunction with drug evaluation protocols to assess the level of BAT activation for a particular therapy.

The embodiments described herein may be used in conjunction with an imaging system. For illustrative purposes, the depicted embodiments are described in view of a magnetic resonance imaging system. However, it should be understood that other types of imaging modalities may also be appropriate for use with the disclosed techniques. In particular, the imaging system may be implemented with specific imaging routines (e.g., MRI sequences) that are initiated by a user (e.g., a radiologist). Further, the imaging system may perform data acquisition, data construction, and image synthesis. The output of the systems provided herein may include images (including processed images, overlay images, and/or annotated images). Other outputs may include numerical indicators (e.g., numerical values representative of concentrations of $^{13}$C-bicarbonate and [1-$^{13}$C] lactate), graphs, or other types of indicators. Further, the present techniques may be used to determine a volume, presence, and/or level of brown adipose tissue or brown adipose tissue activation. In particular, the acquired images or associated image data may be used as inputs to algorithms or protocols for such determinations.

Accordingly, referring to FIG. 1, a magnetic resonance imaging system 10 is illustrated schematically as including a scanner 12, a scanner control circuit 14, and a system control circuitry 16. According to the embodiments described herein, the MRI system 10 is generally configured to perform MR imaging, such as accelerated imaging sequences. The system 10 additionally includes remote access and storage systems or devices as picture archiving and communication systems (PACS) 18, or other devices such as teleradiology equipment so that data acquired by the system 10 may be accessed on-site or off-site. In this way, acquired data may be acquired, followed by on-site or off-site processing and evaluation. While the MRI system 10 may include any suitable scanner or detector, in the illustrated embodiment, the system 10 includes a full body scanner 12 having a housing 20 through which a bore 22 is formed. A table 24 is moveable into the bore 22 to permit a subject 26 to be positioned therein for imaging selected anatomy within the subject.

The scanner 12 includes a series of associated coils for producing a controlled magnetic field and for detecting emissions from gyromagnetic material within the anatomy of the subject being imaged. A primary magnet coil 28 is provided for generating a primary magnetic field generally aligned with the bore 22. A series of gradient coils 30, 32, and 34 permit controlled magnetic gradient fields to be generated during examination sequences. A radio frequency (RF) coil 36 is provided for generating radio frequency pulses for exciting the gyromagnetic material, such as for spin perturbation or slice selection. A separate receiving coil or the same RF coil 36 may receive magnetic resonance signals from the gyromagnetic material during examination sequences.

The various coils of scanner 12 are controlled by external circuitry to generate the desired field and pulses, and to read emissions from the gyromagnetic material in a controlled manner. In the illustrated embodiment, a main power supply 38 is provided for powering the primary field coil 28. Driver circuit 40 is provided for pulsing the gradient field coils 30, 32, and 34. Such a circuit typically includes amplification and control circuitry for supplying current to the coils as defined by digitized pulse sequences output by the scanner control circuit 14. Another control circuit 42 is provided for regulating operation of the RF coil 36. Circuit 42 will typically include a switching device for alternating between the active and passive modes of operation, wherein the RF coils transmits and receives signals, respectively. Circuit 42 also includes amplification circuitry for generating the RF pulses and for processing received magnetic resonance signals.

Scanner control circuit 14 includes an interface circuit 44 that outputs signals for driving the gradient field coils and the RF coil and for receiving the data representative of the magnetic resonance signals produced in examination sequences. The interface circuit 44 is coupled to a control circuit 46. The control circuit 46 executes the commands for driving the circuit 42 and circuit 40 based on defined protocols selected via system control circuit 16. Control circuit 46 also serves to receive the magnetic resonance signals and performs subsequent processing before transmitting the data to system control circuit 16. Scanner control circuit 14 also includes one or more memory circuits 48 which store configuration parameters, pulse sequence descriptions, examination results, and so forth, during operation. Interface circuit 50 is coupled to the control circuit 46 for exchanging data between scanner control circuit 14 and system control circuit 16. Such data will typically include selection of specific examination sequences to be performed, configuration parameters of these sequences, and acquired data, which may be transmitted in raw or processed form from scanner control circuit 14 for subsequent processing, storage, transmission and display.

System control circuit 16 includes an interface circuit 52 which receives data from the scanner control circuit 14 and transmits data and commands back to the scanner control circuit 14. The interface circuit 52 is coupled to a control circuit 54 which may include a CPU in a multi-purpose or application specific computer or workstation. Control circuit 54 is coupled to a memory circuit 56 to store programming code for operation of the MRI system 10 and to store the processed image data for later reconstruction, display and transmission. For example, the programming code may execute one or more algorithms capable of performing accelerated imaging sequences and processing image data, which will be discussed in detail below. An additional interface circuit 58 may be provided for exchanging image data, configuration parameters, and so forth with external system components such as remote access and storage devices 18. Finally, the system control circuit 54 may include various peripheral devices for facilitating operator interface and for producing hard copies of the reconstructed images. In the illustrated embodiment, these peripherals include a printer 60, a monitor 62, and user interface 64 including devices such as a keyboard or a mouse.

Scanner 12 and the control circuit 46 associated therewith produce magnetic fields and radio frequency pulses in a controlled manner to excite and encode specific gyromagnetic material within the subject 26. The scanner 12 and control circuit 46 also sense the signals emanating from such material and create an image of the material being scanned. It should be noted that the MRI system described is merely intended to be an example only, and other system types, such as "open" MRI systems may also be used. Similarly, such systems may be rated by the strength of their primary magnet, and any suitably rated system capable of carrying out the data acquisition and processing described below may be employed.

Specifically, aspects of the present disclosure include methods for acquisition of imaging data and the processing of such data to construct a desired (e.g., a computationally and/or diagnostically-useful) image. At least a portion of the disclosed methods may be performed by the system 10 described above with respect to FIG. 1. That is, the MRI system 10 may perform the acquisition techniques described herein, and, in some embodiments, the data processing techniques described herein. It should be noted that subsequent to the acquisitions described herein, the system 10 may simply store the acquired data for later access locally and/or remotely, for example in a memory circuit (e.g., memory 56). Thus, when accessed locally and/or remotely, the acquired data may be manipulated by one or more processors contained within an application-specific or general purpose computer. The one or more processors may access the acquired data and execute routines including the image processing and reconstruction methods described herein.

Figure 2:
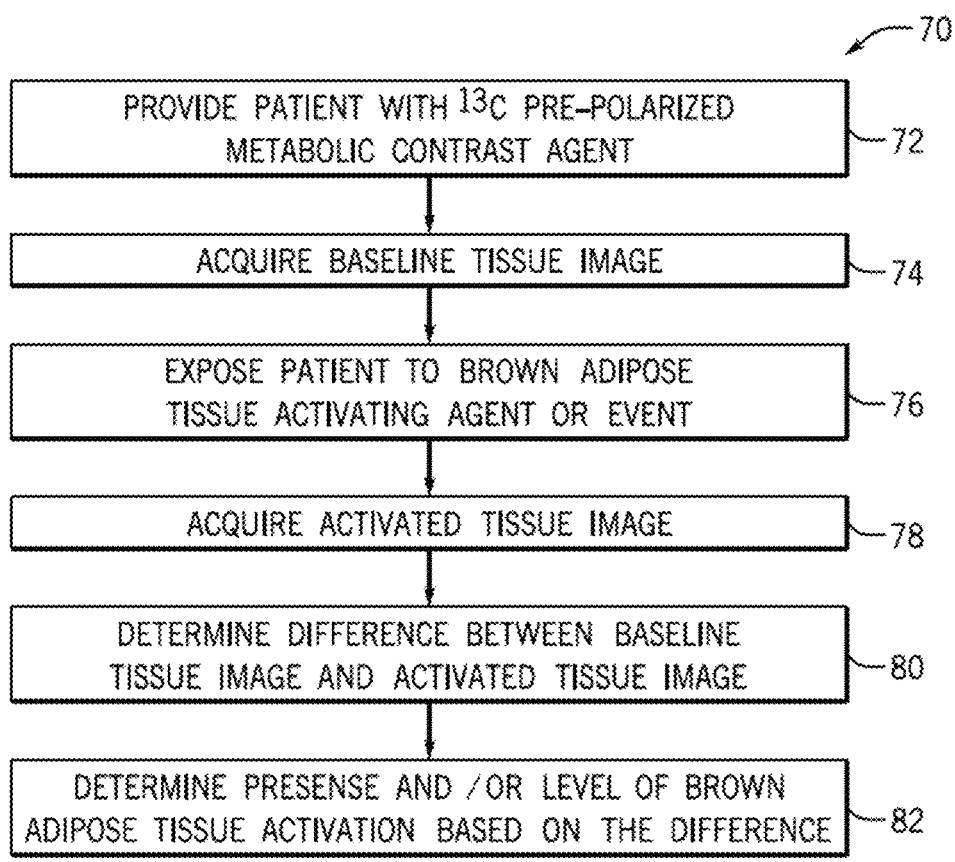
FIG. 2 is a process flow diagram of an embodiment of a method for assessing brown adipose tissue activation.

FIG. 2 illustrates an embodiment of a method 70 of brown adipose tissue assessment and/or identification that may be performed in conjunction with the system 10. The method 70 includes certain steps that may be performed by a caregiver and/or imaging technician as well as steps that may be performed by the system 10. The method begins at step 72 with administration of a $^{13}$C-metabolic contrast agent or other type of metabolic contrast agent to a subject and acquisition of a baseline tissue image at step 74. In certain embodiments, a reference image may be acquired before administration of the $^{13}$C-metabolic contrast agent. For example, the reference image may be used to remove background noise from the baseline image (e.g., via subtraction). In other embodiments, the reference images may be used to clarify locations of identified brown adipose tissue deposits, e.g., via registration with metabolic contrast agent images. For example, the reference images may be standard magnetic resonance images. Further, in one embodiment, the baseline images (alone or in combination with the reference images) may be used to determine a volume and/or presence of brown adipose tissue. In one example, a difference between a baseline and reference image may be used to make such a determination.

Providing or administering the $^{13}$C-metabolic contrast agent may include administering (e.g., via intravenous injection) a pre-polarized $^{13}$C-metabolic contrast agent. After administration, the pre polarized $^{13}$C-metabolic contrast agent enters the appropriate metabolic pathways and is converted to a hyperpolarized $^{13}$C-metabolic contrast agent. The $^{13}$C-metabolic contrast agents may include biomolecules that play a role in the metabolic processes in the human and non-human animal body. For example, the $^{13}$C-metabolic contrast agents may be endogenous compounds such as pyruvate. Pyruvate is an endogenous compound that is very well tolerated by the human body, even in relatively high concentrations. As a precursor in the citric acid cycle, pyruvate plays an important metabolic role in the human body. Pyruvate is converted into different compounds: its transamination results in alanine, via oxidative decarboxylation; pyruvate is converted into acetyl-CoA and carbon dioxide (which is further converted to bicarbonate), the reduction of pyruvate results in lactate and its carboxylation in oxaloacetate.

In certain embodiments, the present techniques may include images of one or more metabolites of $^{13}$C-pyruvate, including hyperpolarized $^{13}$C-lactate, hyperpolarized $^{13}$C-bicarbonate (in the case of 13$C_1$-pyruvate, $^{13}C_{1,2}$-pyruvate or $^{13}C_{1,2,3}$-pyruvate) and hyperpolarized $^{13}$C-alanine can be used to study metabolic processes in the human body using MR. $^{13}C_1$-pyruvate has a T.sub.1 relaxation in human full blood at 37 degrees C. of about 42 s, however, the conversion of hyperpolarized $^{13}$C-pyruvate to hyperpolarized $^{13}$C-lactate, hyperpolarized $^{13}$C-bicarbonate and hyperpolarized $^{13}$C-alanine has been found to be fast enough to allow signal detection from the $^{13}$C-pyruvate parent compound and its metabolites. The amount of alanine, bicarbonate and lactate is dependent on the metabolic status of the tissue under investigation.

The MR signal intensity of hyperpolarized $^{13}$C-lactate, hyperpolarized $^{13}$C-bicarbonate and hyperpolarized $^{13}$C-alanine is related to the amount of these compounds and the degree of polarization left at the time of detection. By monitoring the conversion of pre-polarized $^{13}$C-pyruvate or, in certain embodiments hyperpolarized $^{13}$C-pyruvate, to hyperpolarized $^{13}$C-lactate, hyperpolarized $^{13}$C-bicarbonate and hyperpolarized $^{13}$C-alanine it is possible to study metabolic processes in vivo in the human or non-human animal body by using non-invasive MRI, MRS, or MRSI. Accordingly, the acquired images disclosed herein may be acquired using MRI protocols such as those provided in U.S. Pat. No. 7,550,970 and U.S. Patent Publication No. 2012/0128593, the disclosures of which are incorporated by reference herein in their entirety for all purposes. The terms "hyperpolarized" and "polarized" may denote a nuclear polarization level in excess of 0.1%, in excess of 1%, or in excess of 10%. Certain embodiments of the disclosure involve administration of a pre-polarized metabolic contrast agent, but it should be understood that a metabolic contrast agent that is hyperpolarized may also be administered.

At step 76, the subject is exposed to a brown adipose tissue activating agent or event. For example, a brown adipose tissue activating agent may be an adrenergic agonist, such as epinephrine or norepinephrine. In particular embodiment, the brown adipose tissue activating agent is a compound being tested for potential brown adipose tissue activating ability. In such embodiments, the results of the method 70 may be compared to empirical studies of know brown adipose tissue activating agents. In another embodiment, the brown adipose tissue activating agent or event may include exposure to cold, such as via exposure to a cold jacket. In one embodiment, the cold exposure may reduce skin temperature without significantly reducing (e.g., less than 1-2 degrees C.) core body temperature. At step 78 an activated tissue image is acquired after administration of the brown adipose tissue activating agent and/or event. The time lapse between the administration of the metabolic contrast agent at step 72 and the image acquisition of the baseline image at step 74 may be short (e.g., may be 1-2 minutes). The time lapse between the exposure to the brown adipose tissue activating agent and/or event at step 76 to the activated tissue image acquisition at step 78 may vary, depending on the mechanism of brown adipose tissue activation. For example, cold exposure may take 1-2 hours while norepinephrine stimulation may take 5-20 minutes.

At step 80, after the baseline tissue image and the activated tissue images are acquired, the image data may be analyzed to determine a difference between the images and a corresponding presence and/or level of brown adipose tissue activation at step 82. For example, in one embodiment, the image data may be used without image reconstruction to determine the difference. In another embodiment, the baseline tissue image may be subtracted from the activated tissue image to determine a level of activation and the locations of brown adipose tissue. To that end, the images may be one or more images of tissue suspected of including brown adipose tissue, such as the heart, kidneys, and interscapular region, among others. Further, the present techniques may be used to assess other tissue areas to determine if brown adipose tissue is present.

In certain embodiments, one or both of the baseline and activated tissue images may be acquired after administration of the brown adipose tissue activating agent and/or event. For example, the baseline and activated tissue images may be acquired at different timepoints after the administration, e.g., the baseline images may represent an earlier time point than the activated images, and the timepoints may depend on the characteristics of the brown adipose tissue activating agent and/or event. In another embodiment, activated tissue images, when used alone to determine a presence or volume of brown adipose tissue (e.g., when the activated tissue images are the only metabolic contrast agent images acquired and, for example, may serve as the baseline images), may be acquired after administration of the brown adipose tissue activating agent and/or event at one or more timepoints. Further, at least one of the timepoints may be selected at an estimated maximium brown adipose tissue activation time.

Experimental Results

The following experimental results are from studies using male Sprague-Dawley rats (n=5, weight=336 g, SD=66 g) that were assessed for brown adipose tissue activation and assessment according to certain embodiments of the disclosure. The animals were kept at an ambient room temperature of 22° C. Ketamine/xylazine was used for anesthesia, with periodic intramuscular re-administration to maintain anesthesia (80-100 mg/kg ketamine, 8-10 mg/kg xylazine). Blood oxygen saturation and heart rate were monitored using a peripheral pulse oximeter placed on the tail. The body temperature of the animal was maintained throughout the imaging procedures using a heated water pad.

The animals were scanned in the supine position using a 3T GE MR750 scanner (GE Healthcare, Waukesha, Wis.). A micro-strip dual-tuned $^1$H/$^{13}$C rat coil (Magvale, San Francisco, Calif.) was used. The rat was positioned so that the heart was in the centre of the coil, taking care to position the dorsal interscapular fat pad to remain within the sensitive region of the coil. A $T_2$-weighted fast spin echo (FSE) (TE, 87 ms; TR, 5 s; matrix size, 192×160; FOV, 12×12 cm$^2$; slice thickness, 3 mm) sequence was used to obtain an anatomical reference for co-registration. A 2D FSE IDEAL sequence (TR, 5 s; matrix size, 192×160; FOV, 12×12 cm$^2$, slice thickness, 3 mm) was used to obtain water and fat images.

Hyperpolarized $^{13}$C MR imaging scans were performed following intravenous tail vein infusions of 2.0 mL/80 mM pre-polarized [1-$^{13}$C] pyruvate. Pyruvate was injected over 10 seconds, with the MR imaging acquisition started simultaneously with the start of injection. Hyperpolarized scans were performed during baseline (n=5) and stimulated (n=3) conditions, 15 minutes after 2.5 mg/kg intraperitoneal norepinephrine (NE) injection, separated by approximately 1 hour to prepare the hyperpolarized sample. Pyruvate, bicarbonate, and lactate were imaged in an axial orientation using a multi-slice, single-shot, time-resolved 13C spiral imaging pulse sequence previously developed for large animal cardiac imaging (TR, 5 s; FOV, 48×48 cm$^2$; in-plane resolution, 6.8×6 8 mm$^2$; 6 slices, slice thickness/spacing, 10 mm/1 mm; pyruvate FA 10°, bicarbonate and lactate FA 60°; scan time, 1 min) (18, 24, 25). Each metabolic volume was acquired once during each TR, giving a total of 12 frames.

ROIs were drawn using the $T_2$-weighted anatomical images, over the heart, kidneys, and in the dorsal interscapular region, a known depot of BAT in rodents. The $^{13}$C image intensity in these ROIs were normalized to the temporal maximum pyruvate signal in the heart, and corrected for nominal FA by dividing by sin(FA). Statistical significance between baseline and norepinephrine stimulated conditions were assessed using a two-tailed, unpaired Student's t-test. Statistical significance was considered at the P<0.05 level.

The animals were sacrificed following the second pre-polarized [1-$^{13}$C] pyruvate infusion. The interscapular fat pad was located using a fiducial marker on the anatomical MR images. To confirm that the soft tissue identified as brown adipose tissue using MRI was interscapular BAT, histologic evaluation with hematoxylin-eosin staining was used. Briefly, the torso was removed and prepared for histological sectioning by formalin fixation with bone decalcification. Axial sections (slice thickness, 4 mm) were cut from the fixed tissue, embedded in paraffin, and 5 µm thick slides were prepared for staining. The axial sections were manually coregistered to the corresponding $T_2$-weighted anatomical MR image.

Figure 3:
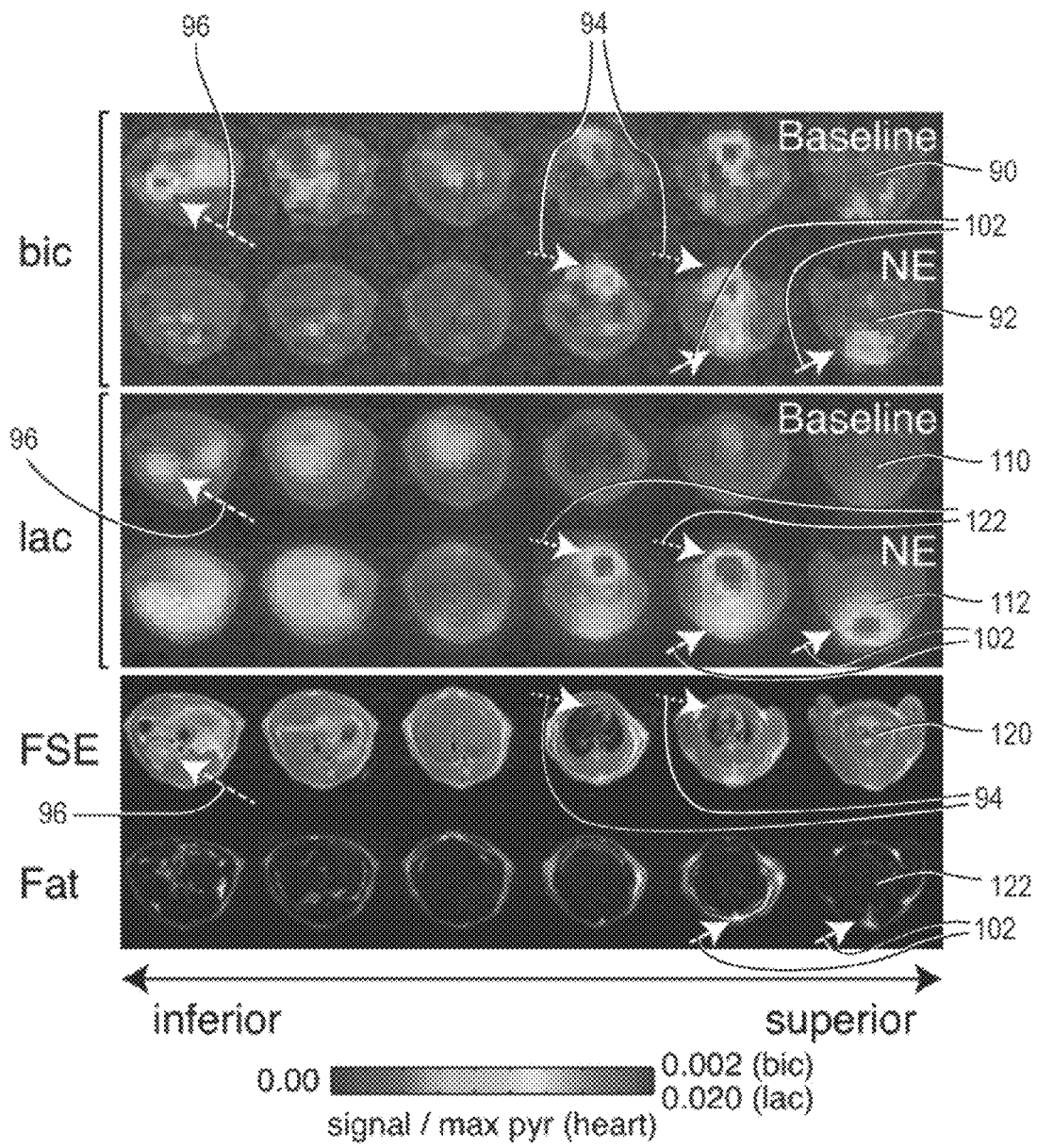
FIG. 3 shows in vivo axial images at baseline and after norepinephrine stimulation of rat tissue.

Representative axial images at baseline and 15 minutes following intraperitoneal norepinephrine stimulation are shown in FIG. 3. Each row contains a series of images from the inferior to superior aspect of the rat. The $^{13}$C images were taken from the time point following hyperpolarized [1-$^{13}$C] pyruvate infusion with maximum metabolite signal in the BAT-associated dorsal interscapular region, and image intensities are normalized to the maximum $^{13}$C pyruvate signal in the heart. $^1$H $T_2$-weighted FSE 120 and IDEAL-reconstructed fat images 122 are shown as anatomical references. Solid arrows 102 indicate a dorsal interscapular BAT depot. Short dashed arrows 94 indicate the heart. Long dashed arrows 96 indicate the right kidney. Images are cropped to 6×6 cm$^2$. The color scale indicates metabolite signal normalized to the maximum cardiac pyruvate signal. Bic denotes hyperpolarized $^{13}$C bicarbonate (baseline 90 and after NE stimulation 92), lac denotes hyperpolarized [1-$^{13}$C] lactate (baseline 110 and after NE stimulation 112).

At baseline, hyperpolarized $^{13}$C bicarbonate was observed in the kidney and in the heart. Following norepinephrine stimulation, $^{13}$C bicarbonate signal decreased in the kidney, remained constant in the heart, and increased in the BAT-associated dorsal interscapular region, relative to substrate signal in the heart. At baseline, hyperpolarized [1-$^{13}$C] lactate was observed in the kidneys, heart, and in the dorsal interscapular region. Increases in all three regions were observed following norepinephrine infusion.

Figure 4:
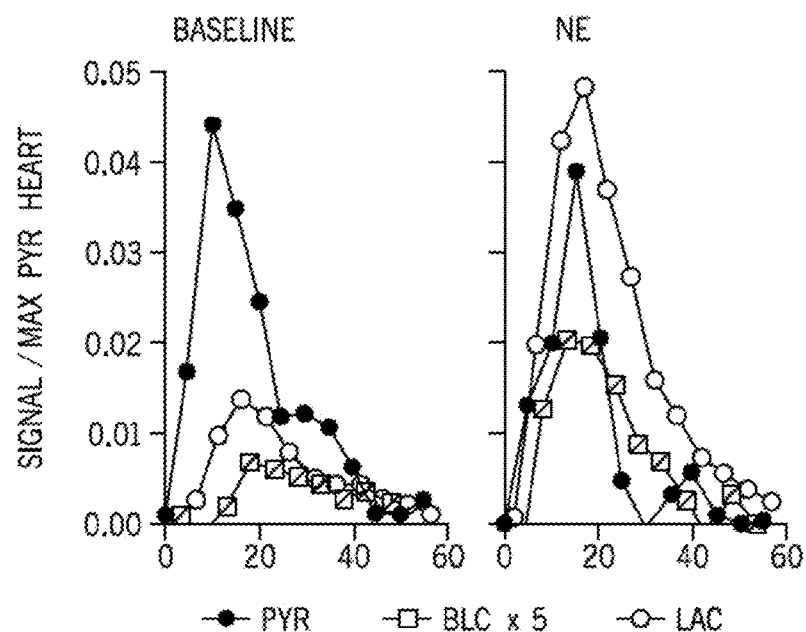
FIG. 4 is a plot of brown adipose tissue metabolite concentration over time at baseline (pre norepinephrine-exposure) and after norepinephrine exposure.

FIG. 4 shows representative metabolic time courses at baseline and following NE stimulation for hyperpolarized $^{13}$C bicarbonate, [1-$^{13}$C] lactate (, and [1-$^{13}$C] pyruvate (signals in the BAT-associated dorsal interscapular region. The signals are divided by the temporal maximum [1-$^{13}$C] pyruvate signal in the heart, to normalize for scan-to-scan differences in substrate polarization and transmit power, as well as for changes in subject positioning and heart rate.

Figure 5A:
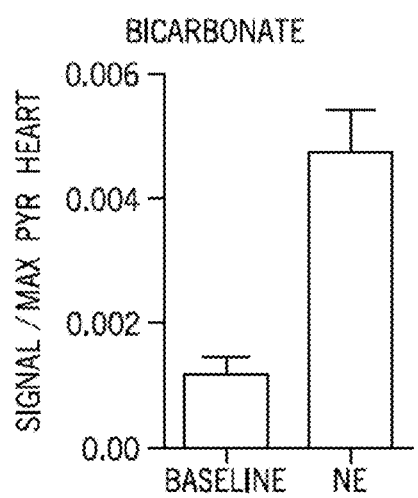
FIG. 5A is a graph of bicarbonate levels before and after norepinephrine exposure.
Figure 5B:
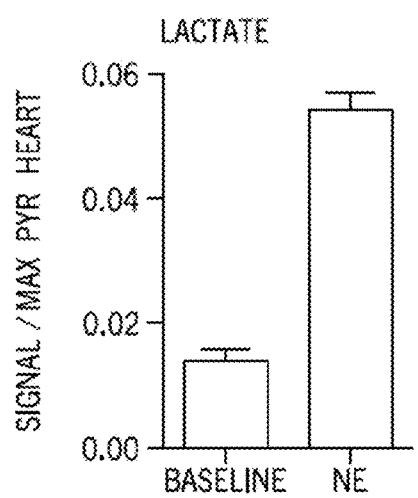
FIG. 5B is a graph of lactate levels before and after norepinephrine exposure.

FIG. 5A and FIG. 5B show metabolite ratios in the BAT-associated dorsal interscapular region, at baseline and following norepinephrine stimulation for bicarbonate (FIG. 5A) and lactate (FIG. 5B). Bicarbonate- and lactate-to-pyruvate ratios (maximum metabolite signal divided by maximum cardiac pyruvate signal) were compared between the two conditions. Statistically significant increases in hyperpolarized $^{13}$C bicarbonate (4.3-fold, P<0.01) and hyperpolarized [1-$^{13}$C] lactate (4.0-fold, P<0.001) in the BAT-associated interscapular region were observed. In one animal, the hyperpolarized 13C bicarbonate signal was undetectable in BAT at baseline and following NE stimulation, indicating low PDH flux; this data was discarded. Hyperpolarized [1-$^{13}$C] lactate signal was detected in all animals at both baseline and following NE stimulation. The ratios were calculated by dividing the metabolite signal by the maximum cardiac pyruvate signal. The difference between the two conditions was significant for both metabolites (P<0.01).

Table 1 summarizes hyperpolarized bicarbonate and lactate ratios measured in the BAT-associated interscapular region, as well as in the heart and kidneys. In addition to the metabolic changes in the interscapular region, significant increases in hyperpolarized lactate signal in the heart (4.0-fold, P<0.001) and the kidneys (1.9-fold, P<0.05) were observed. There was a trend towards higher hyperpolarized bicarbonate signal in the heart, but the difference was not statistically significant. Values are mean±SD. Significant differences in bicarbonate-pyruvate ratio between baseline and norepinephrine stimulated states were observed in the interscapular region (*P<0.01). Significant differences in lactate-pyruvate ratio between baseline and norepinephrine stimulated states were observed in all three regions (†P<0.001, ‡P<0.05).

Figure 6:
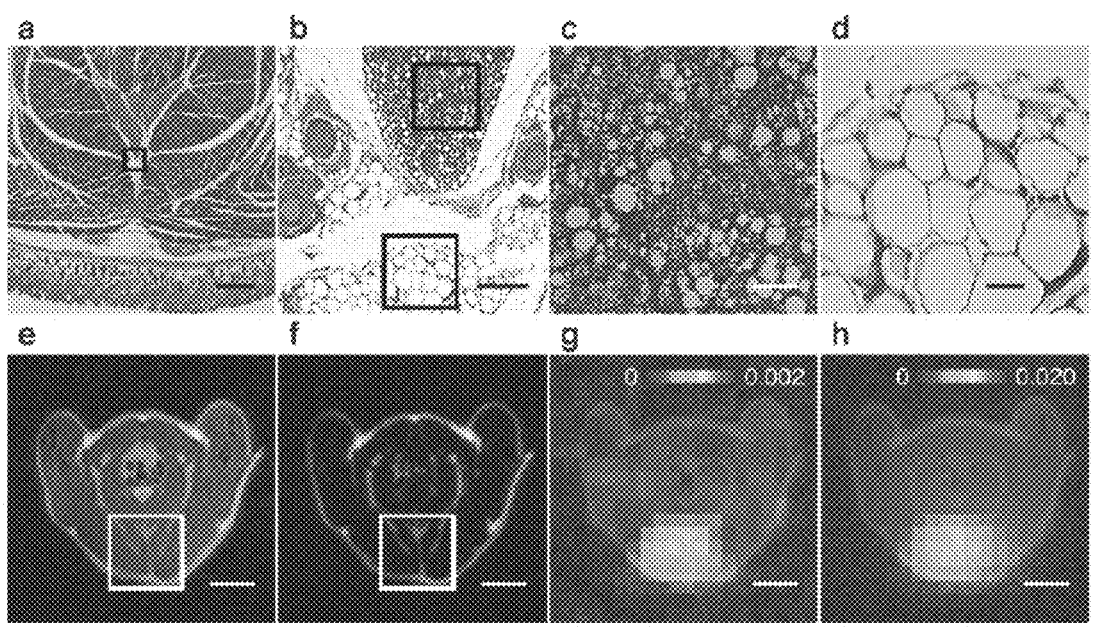
FIG. 6A is a stained section of brown adipose tissue in the dorsal interscapular region at 8× magnification.
FIG. 6B is a stained section of brown adipose tissue in the dorsal interscapular region at 50× magnification.
FIG. 6C is a stained section of brown adipose tissue in the dorsal interscapular region at 400× magnification.
FIG. 6D is a stained section of white adipose tissue in the dorsal interscapular region at 100× magnification.
FIG. 6E is an MR $T_2$-weighted image of brown adipose tissue in the dorsal interscapular region.
FIG. 6F is an MR spin-echo IDEAL fat image of brown adipose tissue in the dorsal interscapular region.
FIG. 6G is an MR post-NE hyperpolarized $^{13}$C-bicarbonate image of brown adipose tissue in the dorsal interscapular region.
FIG. 6H is an MR post-NE hyperpolarized [1-$^{13}$C] lactate image of brown adipose tissue in the dorsal interscapular region.

FIGS. 6A-H display representative hematoxylin-eosin stained axial sections through the dorsal interscapular region, with corresponding T$_2$-weighted MR images at the same axial spatial location. A large depot of interscapular brown adipose tissue was identified (FIG. 6A), along with dispersed brown adipocytes in a white adipose tissue depot underneath the skin. Brown adipose tissue is characterized by a multilocular appearance with multiple intracellular lipid droplets (FIGS. 6B and 6C)), which is distinct from the single intracellular lipid droplets found in white adipose tissue (FIG. 6D). Corresponding anatomical MR images obtained using conventional T$_2$-weighted FSE (FIG. 6E) and IDEAL-reconstructed fat images (FIG. 6F) show close correspondence to the histological sections. Hyperpolarized $^{13}$C bicarbonate (FIG. 6G) and [1-$^{13}$C] lactate (FIG. 6H) obtained following NE stimulation show increased metabolite signal in the BAT-associated dorsal interscapular region, with minimal background signal in the remainder of the slice.

FIG. 6A is at a 8× magnification, scale bar 2 mm; FIG. 6B is at a 50× magnification, scale bar 200 μm; FIG. 6C is at a 400× magnification, scale bar 40 μm; FIG. 6D is white adipose tissue, 100× magnification, scale bar 40 μm. Brown adipose tissue, characterized by a multilocular appearance with multiple intracellular lipid droplets, is found predominantly in a localized depot in the interscapular fat pad. The bottom row shows axial MR images obtained in the same spatial location (scale bars 1 cm): FIG. 6E T$_2$-weighted spin-echo, FIG. 6F spin-echo IDEAL fat image, FIG. 6G post-NE stimulation hyperpolarized $^{13}$C bicarbonate, and FIG. 6H post-NE stimulation hyperpolarized [1-$^{13}$C] lactate.

Hematoxylin-eosin staining of axial sections containing the BAT-associated dorsal interscapular region confirmed the presence of brown adipose tissue. FIGS. 6A-H demonstrate detection of increased hyperpolarized $^{13}$C bicarbonate and lactate signal, co-localized to BAT, following norepinephrine stimulation. In the axial slice shown, the largest and only BAT depot is found in the interscapular region. Thus, increased signal in this region, along with minimal background signal in the remainder of the slice suggests that the increased hyperpolarized $^{13}$C metabolite signal arises from activated BAT. Cryosection or in vivo stereotactic biopsy samples may assist in the identification and registration of the histology data to the MR imaging data. $^{13}$C images may be obtained with relatively coarse resolution to ensure adequate SNR in the images, but as voxel size decreases, improved registration of the data may become more important for validation.

The increases in hyperpolarized $^{13}$C bicarbonate and lactate signals associated with interscapular BAT are consistent with elevated carbohydrate metabolism, as indicated by increased glucose uptake measured using FDG-PET, in activated BAT. Moreover, hyperpolarized $^{13}$C MR enables the in vivo investigation of the metabolic fate of pyruvate beyond uptake. Increased hyperpolarized $^{13}$C bicarbonate signal

TABLE 1

Maximum bicarbonate and lactate to maximum cardiac pyruvate signal ratios in the BAT-associated dorsal interscapular region, the heart, and in the kidneys.

| | Bicarbonate | | Lactate | |
|---|---|---|---|---|
| Region | Baseline (n = 4) | Norepinephrine (n = 2) | Baseline (n = 5) | Norepinephrine (n = 3) |
| Interscapular region | 0.0011 ± 0.0005 | 0.0047 ± 0.0010* | 0.0135 ± 0.0039 | 0.0543 ± 0.0051† |
| Heart | 0.0062 ± 0.0026 | 0.0099 ± 0.0032$^{ns}$ | 0.0202 ± 0.0057 | 0.0816 ± 0.0191‡ |
| Kidney | 0.0069 ± 0.0027 | 0.0036 ± 0.0028$^{ns}$ | 0.0325 ± 0.0162 | 0.0625 ± 0.0130‡ |

(4.3-fold) associated with interscapular BAT is consistent with increases in oxygen consumption upon stimulation. Presumably, increased bicarbonate signal (generated from [1-$^{13}$C] pyruvate) indicates increased TCA cycle flux, which contributes to non-shivering thermogenesis mediated via mitochondrial uncoupling protein (UCP1).

Approximately 10-fold higher [1-$^{13}$C] lactate signal was observed compared to $^{13}$C bicarbonate signal in BAT-associated regions, consistent with the majority of pyruvate taken up by brown adipocytes being converted to lactate via lactate dehydrogenase. Increased lactate signal may indicate additional aerobic and anaerobic glycolytic capacity in BAT. Given the high hyperpolarized [1-$^{13}$C] lactate signal-to-noise ratio in BAT at both baseline and following NE stimulation, increased lactate signal is a reliable marker of activated BAT, in vivo. In the heart, hyperpolarized $^{13}$C bicarbonate signal remained constant relative to substrate signal ($P>0.05$), indicating preserved apparent PDH flux. Hyperpolarized [1-$^{13}$C] lactate signal increased 4.0-fold ($P<0.001$), consistent with a workload-dependent increase in cardiac glycolytic metabolism with NE stimulation.

The imaging pulse sequence used was designed to interrogate [1-$^{13}$C] pyruvate, $^{13}$C bicarbonate, and [1-$^{13}$C] lactate. Additional information may be provided by probing other metabolites derived from [1-$^{13}$C] pyruvate. For example, pyruvate undergoes conversion to the amino acid alanine, in a reaction catalyzed by alanine transaminase (ALT). In vivo studies of pyruvate-alanine metabolism in BAT are limited, but following norepinephrine stimulation, in vitro alanine utilization in isolated BAT decreases. Brown adipocytes also express pyruvate carboxylase, which is a key enzyme involved in gluconeogenesis as well as anaplerotic reactions regenerating TCA cycle intermediates. The $^{13}$C labeled metabolites generated through the pyruvate carboxylase pathway include oxaloacetate, malate, and aspartate, and these metabolites are visible (in the liver) using hyperpolarized $^{13}$C techniques. The role of pyruvate carboxylase may be important in replenishing oxaloacetate for increased TCA cycle flux.

BAT is highly vascularized and is richly innervated by the sympathetic nervous system. Norepinephrine, a potent stimulator of the sympathetic nervous system, may be used to stimulate non-shivering thermogenesis and activate BAT in vivo. The dose and imaging time point (15 minutes following NE injection) was based on a related study investigating oxygen consumption in mice. Systemic injection of norepinephrine has a myriad of physiological effects caused by simultaneous stimulation of all adrenergic receptors in the body, and adverse effects on the cardiovascular system as well as other organ systems has prevented administration in humans. Other methods for activating BAT in vivo include cold stimulation (non-shivering thermogenesis) and eating (diet-induced thermogenesis). For example, fasting is known to inactivate BAT activity in vivo.

Hyperpolarized $^{13}$C studies of metabolism provide data related to metabolic fluxes, in vivo. Following infusion of pre-polarized [1-$^{13}$C] pyruvate, the hyperpolarized $^{13}$C bicarbonate signal is a measure of PDH flux. The hyperpolarized [1-$^{13}$C] lactate signal is a measure of both flux through the LDH enzyme as well as a measure of the pre-existing lactate pool size due to the reversible two-way exchange reaction catalyzed by LDH. Thus, hyperpolarized [1-$^{13}$C] pyruvate has the potential to provide additional metabolic information beyond glucose uptake, as provided by FDG-PET.

The increased hyperpolarized signal seen in the dorsal interscapular region was due to an increase in metabolic enzyme activity. To separate the effect from the effect of a change in perfusion, the dynamic data was fit on a voxel-by-voxel basis to obtain the apparent rate constants for pyruvate-to-bicarbonate conversion ($k_{pyr,bic}$, s$^{-1}$) and pyruvate-to-lactate exchange ($k_{pyr,lac}$, s$^{-1}$). Significant differences in apparent pyruvate-to-bicarbonate and pyruvate-to-lactate conversion rates (3.4-fold and 4.0-fold, respectively) were observed in the BAT-associated dorsal interscapular region. These results suggest that the increased hyperpolarized metabolite signal observed following NE stimulation is due, in part, to increased metabolic activity, in addition to increased perfusion of the tissue (for example, via increased PDH or LDH flux, as well as through increased monocarboxylate transporter activity).

[1-$^{13}$C] pyruvate and its major observable downstream metabolites in vivo (lactate and bicarbonate) can be imaged using the imaging approach provided herein. Alternative labeling patterns may provide additional information regarding BAT metabolism. Probing TCA cycle flux may inform not only on carbohydrate metabolism but also on fatty acid metabolism in BAT. Pre-polarized [2-$^{13}$C] pyruvate can be used as a substrate to probe TCA cycle flux by measuring the appearance of [5-$^{13}$C] glutamate. In particular, pyruvate shares a similar metabolic fate as free fatty acids following conversion to acetyl-CoA. In this sense, measuring metabolic fluxes from a carbohydrate substrate may provide information related to fatty acid metabolism in brown adipose tissue, aiding the development of agents that activate BAT in vivo.

Furthermore, alternative hyperpolarized substrates may be of interest to probe BAT metabolism. Fatty acids are the primary substrate in BAT for oxidative metabolism, contributing approximately 90% to total oxygen consumption. This proportion increases even further in the stimulated state (glucose requiring approximately 2% of total oxygen consumption), indicating that pre-polarized fatty acids may be a more sensitive substrate for probing TCA cycle reactions in activated brown adipose tissue. Accordingly, the present techniques may be used in conjunction with pre-polarized and/or hyperpolarized fatty acids as the metabolic contrast agents. For example, pre-polarized [1-$^{13}$C] butyrate, a four-carbon short chain fatty acid, has been hyperpolarized both directly and via chemical reactions taken place after the hyperpolarization process. The $^{13}$C label on butyrate has a similar $T_1$ relaxation time to that of [2-$^{13}$C] pyruvate, and in vivo beta-oxidation in perfused rat hearts results in visible resonances corresponding to glutamate, beta-hydroxybutyrate, citrate, acetoacetate, and acetylcarnitine. Given the relatively high usage of fatty acids in BAT, this may be a highly specific agent for probing BAT metabolism. The [2-$^{13}$C] pyruvate and [1-$^{13}$C] butyrate contrast agents may be used with imaging methods that spatially resolve the substrate and downstream products in BAT.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:
1. A method for detecting brown adipose tissue, comprising:
    acquiring one or more images of an adipose tissue of a subject representative of a relative level of a pre-polarized metabolic contrast agent, its metabolic products, or a combination thereof;
    acquiring one or more activated tissue images of the subject representative of a relative level of the pre-polarized metabolic contrast agent and/or its metabolic products after exposing the subject to a brown adipose tissue activating agent or event;

determining a difference between the one or more images and the one or more activated tissue images; and determining a presence or volume of brown adipose tissue activation based at least in part on the difference between the one or more images and the one or more activated tissue images.

2. The method of claim 1, wherein the brown adipose tissue activating agent or event comprises administration of an adrenergic agonist.

3. The method of claim 2, wherein the adrenergic agonist comprises norepinephrine.

4. The method of claim 1, wherein the brown adipose tissue activating agent or event comprises a reduction in a core or skin temperature of the subject.

5. The method of claim 1, wherein the brown adipose tissue activating agent or event comprises a reduction in a skin temperature of the subject without a reduction of more than 1-2 degrees C. of core body temperature of the subject.

6. The method of claim 1, comprising identifying one or more locations of brown adipose tissue activation in the subject based on the difference.

7. The method of claim 1, wherein the one or more images and the activated tissue images are taken after the brown adipose tissue activating agent or event that comprises administration of an adrenergic agonist, a reduction in a core or skin temperature of the subject, or a combination thereof.

8. The method of claim 1, wherein the one or more are taken after the brown adipose tissue activating agent or event, wherein the brown adipose tissue activating agent or event that comprises administration of an adrenergic agonist, a reduction in a core or skin temperature of the subject, or a combination thereof.

9. The method of claim 1, wherein the one or more images comprise images of a cervical neck and supraclavicular region, chest, abdomen, or a combination thereof.

10. The method of claim 1, comprising acquiring one or more reference images before administration of the pre-polarized metabolic contrast agent.

11. The method of claim 1, wherein the pre-polarized metabolic contrast agent comprises pre-polarized $[1^{13}C]$ pyruvate.

12. The method of claim 1, wherein the metabolic products of the pre-polarized metabolic contrast agent comprise hyperpolarized $^{13}C$-bicarbonate, $[1-^{13}C]$ lactate, or a combination thereof.

13. The method of claim 1, wherein the one or more images are magnetic resonance images.

14. An imaging system, comprising:

a processor configured to receive and process image data, wherein in the processor is configured to:

receive a baseline tissue image of a subject with a $^{13}C$ metabolic contrast agent in a bloodstream of the subject;

receive an activated tissue image of a subject with the $^{13}C$ metabolic contrast agent in the bloodstream of the subject after exposing the subject to a brown adipose tissue activating agent or event, wherein the baseline tissue image and the activated tissue image are representative of a concentration of one or more hyperpolarized $^{13}C$ products of the $^{13}C$ metabolic contrast agent;

determine a difference between the baseline tissue image and the activated tissue image; and determine a level or presence of brown adipose tissue activation based at least in part on the difference; and a display coupled to the processor and configured to provide an indication related to the level or presence of brown adipose tissue activation.

15. The system of claim 14, wherein the processor is configured to receive a reference tissue image of the subject without the $^{13}C$ metabolic contrast agent in the bloodstream of the subject.

16. The system of claim 14, wherein the baseline images and the activated tissue images are taken at different time points after exposing the subject to a brown adipose tissue activating agent or event.

17. An imaging method, comprising:

injecting a pre-polarized $^{13}C$ metabolic contrast agent into a bloodstream of a subject;

exposing the subject to a brown adipose tissue activating agent or event; and providing one or more inputs to an imaging system to instruct the imaging system to obtain a plurality of images of the subject, wherein the images comprise a baseline tissue image and an activated tissue of the subject, wherein the baseline image is obtained before exposing the subject to the brown adipose tissue activating agent or event and the activated tissue image is acquired after exposing the subject to the brown adipose tissue activating agent or event.

18. The method of claim 17, comprising providing an indication to the subject related to a presence or level of activated brown adipose tissue.

19. The method of claim 17, wherein the images are images representative of a hyperpolarized metabolic product of the pre-polarized 13C metabolic contrast agent.

* * * * *